United States Patent
Koen et al.

(10) Patent No.: US 8,715,192 B2
(45) Date of Patent: *May 6, 2014

(54) HIGH VOLTAGE ULTRASOUND TRANSMITTER WITH SYMMETRICAL HIGH AND LOW SIDE DRIVERS COMPRISING STACKED TRANSISTORS

(75) Inventors: Myron J. Koen, Tucson, AZ (US); Ismail H. Oguzman, Plano, TX (US)

(73) Assignee: Texas Instruments Incorporated, Dallas, TX (US)

( * ) Notice: Subject to any disclaimer, the term of this patent is extended or adjusted under 35 U.S.C. 154(b) by 661 days.

This patent is subject to a terminal disclaimer.

(21) Appl. No.: 12/261,252

(22) Filed: Oct. 30, 2008

(65) Prior Publication Data

US 2010/0113935 A1    May 6, 2010

(51) Int. Cl.
*A61B 8/00*    (2006.01)

(52) U.S. Cl.
USPC ............................. 600/459; 310/317

(58) Field of Classification Search
CPC .................................................. B06B 1/0215
USPC ............. 326/83, 84; 327/206, 248, 108; 600/437, 459, 443; 310/334; 330/136, 330/253, 254, 298, 69, 9; 324/673, 762.09
See application file for complete search history.

(56) References Cited

U.S. PATENT DOCUMENTS

| | | | | |
|---|---|---|---|---|
| 3,984,703 A | * | 10/1976 | Jorgensen | 327/206 |
| 4,079,336 A | * | 3/1978 | Gross | 330/296 |
| 4,358,724 A | * | 11/1982 | Haner | 318/681 |
| 4,456,837 A | * | 6/1984 | Schade, Jr. | 327/259 |
| 4,486,670 A | * | 12/1984 | Chan et al. | 326/81 |
| 4,563,595 A | * | 1/1986 | Bose | 327/206 |
| 5,589,800 A | * | 12/1996 | Peterson | 330/288 |
| 6,087,881 A | * | 7/2000 | Chan et al. | 327/333 |
| 6,135,961 A | | 10/2000 | Pflugrath et al. | |
| 6,648,826 B2 | | 11/2003 | Little et al. | |
| 6,705,995 B1 | * | 3/2004 | Poland et al. | 600/447 |
| 6,856,175 B2 | * | 2/2005 | Wodnicki | 327/108 |
| 7,304,415 B2 | * | 12/2007 | Petersen et al. | 310/334 |
| 7,604,596 B2 | | 10/2009 | Hwang et al. | |
| 2003/0163047 A1 | | 8/2003 | Little et al. | |
| 2004/0133110 A1 | | 7/2004 | Little et al. | |
| 2005/0265267 A1 | | 12/2005 | Hwang | |
| 2006/0052697 A1 | * | 3/2006 | Hossack et al. | 600/437 |

(Continued)

OTHER PUBLICATIONS

MD1711, "High Speed, Integrated Ultrasound Driver IC", Supertex Inc, 2005, pp. 1-9.*
Chu, "Designing an Ultrasound Pulser with MD1812/MD1813 Composite Drivers", AN-H56, Supertex Inc, 2005, pp. 1-10.*

(Continued)

*Primary Examiner* — Unsu Jung
*Assistant Examiner* — Serkan Akar
(74) *Attorney, Agent, or Firm* — Alan A. R. Cooper; W. James Brady, III; Frederick J. Telecky, Jr.

(57) ABSTRACT

A system and method for providing a high voltage ultrasonic drive signal from an ultrasound transmitter are disclosed herein. An ultrasound transmitter includes a first driver and a second driver. Each of the drivers includes an N-type device and a P-type device. The N-type device and the P-type device of each driver are serially coupled. Activation of the first driver drives an ultrasound transmitter output to a first voltage. Activation of the second driver drives the ultrasound transmitter output to a second voltage. The driver activations produce an ultrasonic drive signal at the ultrasound transmitter output.

12 Claims, 3 Drawing Sheets

(56) References Cited

U.S. PATENT DOCUMENTS

| | | | |
|---|---|---|---|
| 2006/0170453 A1* | 8/2006 | Zerbe et al. | 326/37 |
| 2006/0176073 A1* | 8/2006 | Chen et al. | 326/21 |
| 2006/0267633 A1* | 11/2006 | King | 326/83 |
| 2007/0016022 A1* | 1/2007 | Blalock et al. | 600/437 |
| 2007/0016044 A1* | 1/2007 | Blalock et al. | 600/443 |
| 2008/0211468 A1* | 9/2008 | Sadwick et al. | 323/272 |
| 2008/0262351 A1* | 10/2008 | Scampini | 600/443 |
| 2010/0012119 A1 | 1/2010 | Sallak et al. | |

OTHER PUBLICATIONS

B. Haider, "Power Drive Circuits for Medical Diagnostic Medical Ultrasound," IEEE Proceedings of the 18th international Symposium on Power Semiconductor Devices and ICs, Jun. 2006.

M. A. Averkiou, D. N. Roundhill and J. E. Powers, "A New Imaging Technique Based on the Nonlinear Properties of Tissues," IEEE Ultrasonics Symposium, 1997.

B. Haider and R. Y. Chiao, "Higher Order Nonlinear Ultrasonic Imaging," IEEE Ultrasonics Symposium, 1999.

* cited by examiner

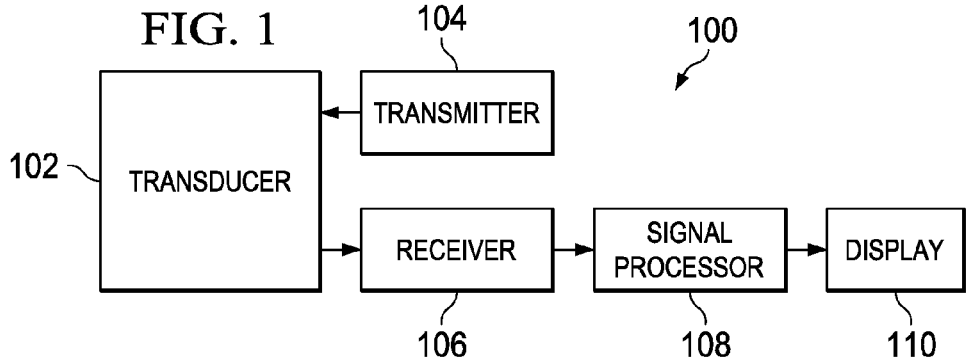
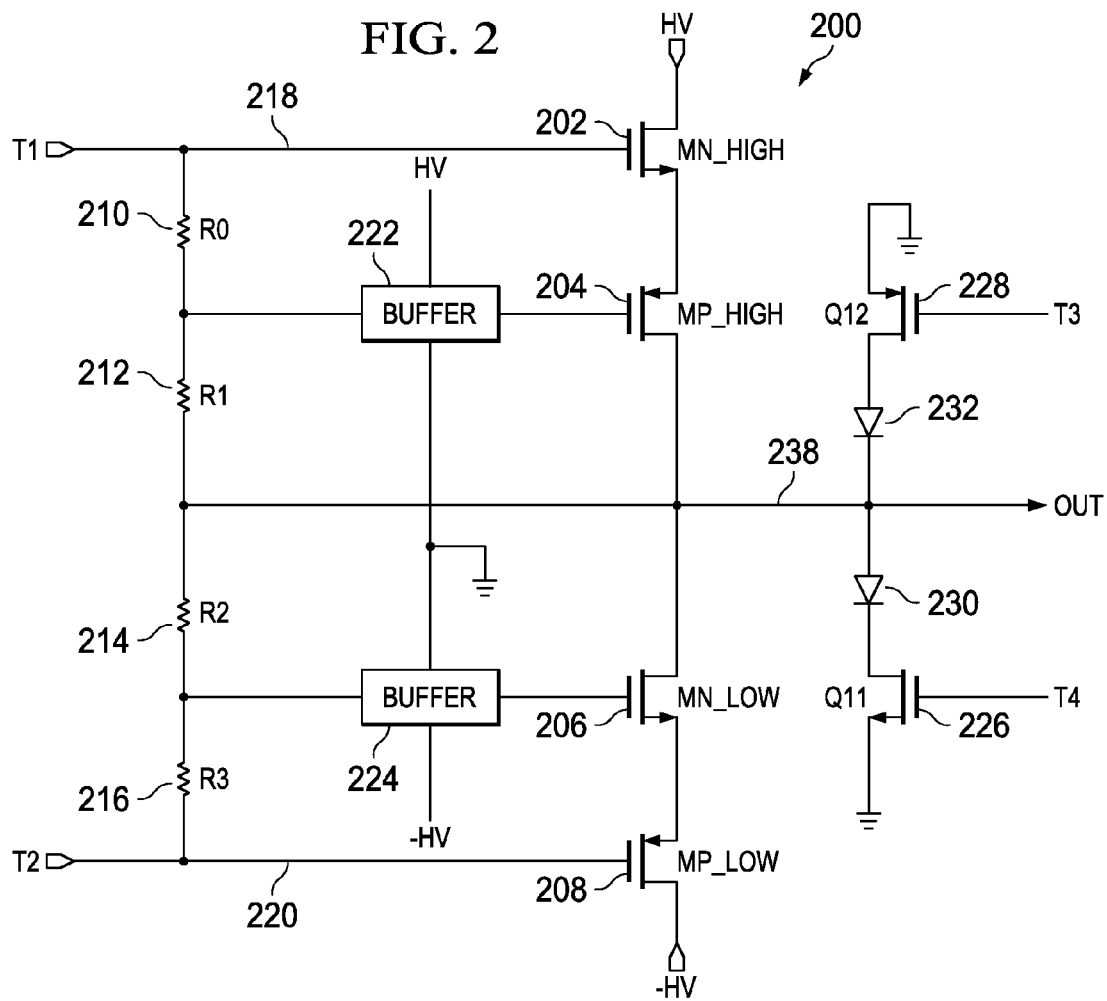

HIGH VOLTAGE ULTRASOUND TRANSMITTER WITH SYMMETRICAL HIGH AND LOW SIDE DRIVERS COMPRISING STACKED TRANSISTORS

CROSS REFERENCE TO RELATED APPLICATIONS

This application contains subject matter that may be related to U.S. patent application Ser. No. 12/261,185, entitled "Low Power Continuous Wave Ultrasound Transmitter", U.S. patent application Ser. No. 12/261,209, entitled "Ultrasound Transmitter", and U.S. patent application Ser. No. 12/261,269, entitled "Ultrasound Transmitter".

BACKGROUND

Ultrasonic imaging has become a widely used tool in medical applications. Ultrasound techniques introduce high-frequency acoustic waves into a subject's body. The received echoes of those waves provide information allowing a trained observer to view the subject's internal organs. Ultrasound imaging equipment uses transducers that convert electrical energy into acoustic energy. Piezo-electric crystals are one commonly used type of electrical to acoustical transducer. To obtain a clear image, a high signal to noise ratio is desirable to overcome random noise associated with the imaging process. One way to increase the signal-to-noise ratio is to increase the amplitude of the signal driving the transducer. Generally, the transducer drive signal may require voltages in the range of +/−75 volts to +/−100 volts.

There are two broad categories of ultrasound transmitters, digital and analog. The analog type takes a signal generated digitally and after being converted to analog form, by a digital to analog converter, the signal is amplified to the required higher voltage by a power amplifier. This type of transmitter is capable of generating complex waveforms by using a high-resolution digital to analog converter with a resolution of, for example, 12 bits. This technique is expensive and finds application in high-end ultrasound imaging systems.

Digital transmitters are simpler and less expensive than analog transmitters. Unfortunately, the semiconductor process technologies used to fabricate digital circuits, which are often less expensive and provide better performance than high voltage processes, do not typically accommodate the high voltages required to produce an acceptable signal-to-noise ratio in an ultrasound imager. Furthermore, users of ultrasound imaging systems demand both power efficiency and portability in modern ultrasound equipment.

SUMMARY

Various systems and methods for implementing a high-voltage ultrasound transmitter are disclosed herein. In accordance with at least some embodiments, an ultrasound transmitter includes a first driver and a second driver. Each of the drivers includes an N-type device and a P-type device. The N-type device and the P-type device of each driver are serially coupled. Activation of the first driver drives an ultrasound transmitter output to a first voltage. Activation of the second driver drives the ultrasound transmitter output to a second voltage. The driver activations produce an ultrasonic drive signal at the ultrasound transmitter output.

In accordance with at least some other embodiments, a method includes activating a first N-type device and a first P-type device connected in series. The devices drive an output node to a first voltage. A second N-type device and a second P-type device are connected in series. When activated, second N-type device and a second P-type device drive the output node to a second voltage. The second N-type device and a second P-type device are deactivated while the first N-type device and the first P-type device are activated.

In accordance with yet other embodiments, an ultrasound imaging system includes an ultrasonic signal transducer that converts an electrical signal into an acoustical signal. A signal transmitter is coupled to the transducer. The transmitter includes a high-side driver. The high-side driver includes a first set of stacked complementary drive transistors. The transmitter provides electrical signals to the transducer.

BRIEF DESCRIPTION OF THE DRAWINGS

For a detailed description of exemplary embodiments of the invention, reference will now be made to the accompanying drawings in which:

FIG. 1 shows a block diagram of an exemplary ultrasound imaging system in accordance with various embodiments;

FIG. 2 shows an exemplary ultrasound transmitter circuit that provides a high voltage output with a symmetrical output configuration in accordance with various embodiments;

NOTATION AND NOMENCLATURE

Figure 3:
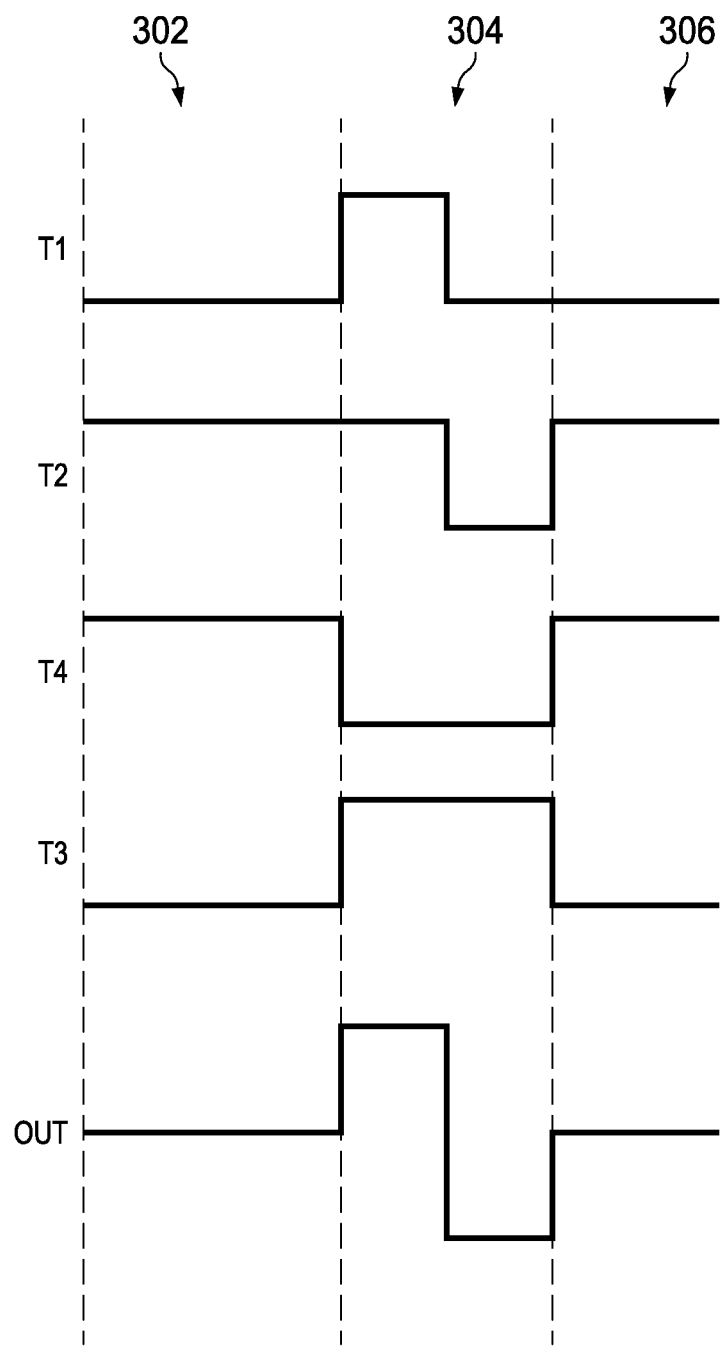
FIG. 3 shows a diagram of various signals produced when generating high voltage ultrasonic drive signals in accordance with various embodiments.

Certain terms are used throughout the following description and claims to refer to particular system components. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct electrical connection. Thus, if a first device couples to a second device, that connection may be through a direct electrical connection, or through an indirect electrical connection via other devices and connections.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

The performance and cost efficiency of low voltage semiconductor processes make it desirable to use those processes to implement high voltage circuits. High voltage circuits can be so implemented by connecting transistors (e.g., field effect transistors ("FETs")) in series (i.e., stacked), and in such a way as to ensure that the voltage across the transistors is distributed in a predictable manner. If transistors are stacked without considering voltage distribution, it may be possible for the voltage across an individual transistor to exceed the process specification. Moreover, a bias network that achieves predictable voltage distribution can result in undesirable power dissipation and/or poor switching performance. Drivers employing stacked transistors can also suffer from an undesirable lack of output symmetry due to process and/or temperature variations. Further, to reduce power dissipation, a low on resistance is needed, requiring the stacked transistors to be large.

Embodiments of the present disclosure employ symmetrically configured high side and low side drivers wherein each driver includes serially connected complementary transistors (i.e., an N-type transistor in series with a P-type transistor in each of the high and low side drivers). Such a configuration advantageously reduces circuit area, provides improved performance across process and temperature, and results in reduced transmitter quiescent power dissipation.

FIG. 1 shows a block diagram of an exemplary ultrasound imaging system 100 in accordance with various embodiments. The system 100 comprises a transducer 102, a transmitter 104, a receiver 106, a signal processor 108, and a display 110. The transducer 102 converts the electrical drive signals generated by the transmitter 104 into sound waves (i.e., pressure waves) that are introduced into the subject to be imaged, for example, a human body when considering medical ultrasound. The transducer 102 can comprise a piezoelectric crystal, electromagnetic transducer, micro-electro-mechanical system ("MEMS") transducer or other device that converts an electrical signal into sound waves. Moreover, the transducer 102 can comprise one or more transducer elements. The transducer 102 also detects ultrasonic waves reflected by internal structures of the subject and converts the detected waves into electrical signals. In some embodiments, the same transducer elements are used to generate ultrasonic waves and to detect ultrasonic waves. In other embodiments, separate transducer elements are used for wave generation and detection.

The transmitter 104 is coupled to the transducer 102. The transmitter 104 produces an oscillating electrical signal at a frequency and amplitude suitable for imaging desired structures internal to the subject. For example, transmitter output signals for use in imaging the internal organs of a human body may range in frequency from 1 to 20 megahertz with lower frequencies providing lower resolution and greater imaging depth. Other applications may use different frequencies. The transmitter 104, while not limited to any particular signal amplitudes, may provide, for example, a drive signal amplitude in the range of +/−75 volts. The transmitter 104 employed in embodiments of the present disclosure advantageously uses transmitter circuitry having symmetrical drivers that allow for efficient implementation of a high voltage ultrasonic driver on a low voltage semiconductor process, while reducing circuit area and power dissipation, and improving performance across temperature and process variation.

The receiver 106 is coupled to the transducer 102. As explained above, the transducer 102 detects ultrasonic waves reflected by subject internal structures. The transducer 102 converts the detected waves into electrical signals. The electrical signals are provided to the receiver 106. The receiver 106 performs initial processing of the received signals. Processing performed by the receiver 106 can comprise, for example, amplifying, filtering, digitizing, etc.

The signal processor 108 is coupled to the receiver 106. The signal processor 108 may, for example, provide post-digitization filtering of received signals, detect signal reflections, and prepare output signals for display on the display 110. The signal processor 108 may comprise, for example, a digital signal processor or other microprocessor or microcomputer and associated software programming along with attendant memory and interface devices, or dedicated hardware circuitry adapted to perform the processing functions. The display 110 may be a liquid crystal display, a cathode ray display, or any other suitable display device.

FIG. 2 shows an exemplary ultrasound transmitter circuit 200 that employs a symmetrical output configuration and provides a high voltage output in accordance with various embodiments. The transmitter 200 is configured to provide symmetry between the high side and the low side of the transmitter 200 output circuitry. Accordingly, the high side driver and the low side driver each include both a P-type transistor and an N-type transistor. The high-side driver comprises N-type transistor MN_HIGH 202 and P-type transistor MP_HIGH 204 connected in series, and the low-side driver comprises N-type transistor MN_LOW 206 and P-type transistor MP_LOW 208 connected in series. When enabled, stacked drive transistors MN_HIGH 202 and MP_HIGH 204 provide high voltage, +HV, to the transmitter output 238. Similarly, stacked drive transistors MN_LOW 206 and MP_LOW 208 provide high voltage, −HV, to the transmitter output 238 when enabled.

The stacked N-type and P-type transistors employed by embodiments of the present disclosure provide a number of advantages. Using an N-type transistor in series with a P-type transistor on both the high and low sides of the transmitter compensates for the lower mobility of the P-type transistor, and results in a smaller circuit area (for example, 15-20% less area) than would be required by an embodiment employing only P-type transistors on one side. Because the characteristics of one transistor type compensate for the characteristics of the other, high/low side symmetry also results in significantly improved performance in less than nominal conditions, for example, at temperature extremes or at process limits. Symmetry can provide a substantial improvement in the harmonic distortion present in the output signal. For example, at the process limits, symmetry can result in as much as a 25% reduction in the second harmonic content of the output with respect to the fundamental when compared to an asymmetrical embodiment.

As explained above, voltage should be predictably distributed across each transistor of a set of stacked transistors. The bias network comprising resistors R0 210, R1 212, R2 214, and R3 216 ensures that voltage is approximately equally distributed across each transistor of transistor pair MN_HIGH 202 and MP_HIGH 204, and each transistor of transistor pair MN_LOW 206 and MP_LOW 208 to assure that the breakdown voltage of the transistors is not exceeded. In some embodiments, for example, the voltage drop across a selected drive transistor may be within 10% of the voltage drop across the other drive transistor of the transistor pair.

In ultrasound applications, the duty cycle of the transmitter 200 can be low (i.e., the transmitter on time is short relative to the transmitter off time). For example, the transmitter 200 duty cycle may be in the range of 1% (i.e., on 1% of the time and off 99% of the time), so that even though the drive transistors 202, 204, 206, 208 may conduct a relatively large amount of current, the large amount of current is required for only a short period of time.

The high side driver, comprising MN_HIGH 202 and MP_HIGH 204, is enabled to provide voltage HV to output 238 by asserting signal T1 218 (i.e., bringing the T1 218 signal voltage near HV). Similarly, the low side driver, comprising MN_LOW 206 and MP_LOW 208, is enabled to provide voltage −HV to output 238 by asserting signal T2 220 (i.e., bringing the T2 220 signal voltage near −HV). Either of the high side or the low side drivers can be disabled by bringing the corresponding control signal (T1 218 or T2 220) near to ground. Thus, when both high and low side drivers are disabled, the voltages present on T1 218 and T2 220 are preferably approximately equal. Consequently, the voltage drop across the bias network comprising R0 210, R1 212, R2 214, and R3 216 can be zero or very small when the transmitter 200 is disabled, resulting in little or no current flow through the bias network. By way of contrast, the current flowing in the bias network of a disabled asymmetrical output driver can be on the order of 10 mA. Such a reduction in quiescent current is significant when the 1% duty cycle of the ultrasound transmitter 200 is considered.

The drive transistors, for example MP_HIGH 204 and MN_LOW 206, can be very large to achieve a low on resistance. Correspondingly, the gate capacitance of large field effect transistors ("FETs") can also be very large. Transmitter 200 preferably comprises buffer drivers 222, 224 to drive the gates of drive transistors MP_HIGH 204 and MN_LOW 206 respectively. The buffer drivers 222, 224 provide current suitable to enable fast switching of the drive transistors MP_HIGH 204 and MN_LOW 206. In some embodiments, the buffers 222, 224 are source followers. Ultrasound transmitter embodiments not incorporating buffers 222, 224 suffer from slower switching of the drive transistors MP_HIGH 204 and MN_LOW 206 and consequently may not provide ultrasonic drive signals at frequencies as high as those produced by embodiments of the present disclosure.

The input capacitance of the buffers 222, 224 is preferably substantially lower than the gate capacitance of the drive transistors MP_HIGH 204 and MN_LOW 206, for example, in some embodiments by approximately a factor of 20 or more. Consequently, in embodiments of the present disclosure, the values of resistors R0-R3 210-216 can be 20 times larger than in an embodiment without the drivers 222, 224. Thus, the current flowing through bias resistors R0-R3 210-216 when the transmitter 200 is active can be 20 times lower than in an embodiment omitting the buffers 222, 224.

Transistors Q11 226, Q12 228, and diodes 230, 232 comprise a clamping circuit that, when enabled, shunts the transmitter output 238 to ground. The clamping circuit is generally enabled when the transmitter 200 is not generating ultrasonic drive signals.

An ultrasonic drive signal is generated by transmitter 200 as follows. The output clamp is disabled by turning off transistors Q11 226 and Q12 228. MN_HIGH 202 and MP_HIGH 204 are turned on and MN_LOW 206 and MP_LOW 208 are turned off to drive the output 238 to +HV. MN_HIGH 202 and MP_HIGH 204 are turned off and MN_LOW 206 and MP_LOW 208 are turned on to drive the output 238 to −HV. Thus, the high and low side drivers are alternately turned on and off at the desired frequency to generate an ultrasonic drive signal on output 238. During intervals when no ultrasonic drive signal is being generated, the high and low side drivers are disabled by bringing T1 218 and T2 220 to ground, and the output 238 is shunted to ground by turning on transistors Q11 226 and Q12 228. Some embodiments activate the output clamp (transistors Q11 226 and Q12 228) between +HV and −HV drive intervals (while both high and low side drivers are disabled) to clamp the output 238 to ground. Some embodiments generate pulses of one polarity by repetitively enabling and disabling only one of the high and low side drivers and enabling clamping when the drive transistors are disabled.

FIG. 3 shows a diagram of various signals produced when generating high voltage ultrasonic drive signals in accordance with various embodiments. The diagram begins, in period 302, with the transmitter driver 200 in shunt mode where the output 238 is clamped to ground through diodes 230, 232 and transistors Q11 226 and Q12 228. Signals T3 and T4 are asserted to enable transistors Q12 228 and Q11 226 respectively. The signals T1 and T2 are negated (i.e., brought to ground), disabling drive transistors MN_HIGH 202, MP_HIGH 204, MN_LOW 206 and MP_LOW 208, and minimizing the current flowing in the bias resistors R0-R3 210-216.

A high voltage ultrasonic drive signal is generated in period 304. To produce the high voltage signal on the output 238, the shunt transistors Q11 226 and Q12 228 are turned off by negating T4 and T3 as illustrated. Thereafter, signals T1 and T2 are toggled as shown to alternately turn on and off high side drive transistors MN_HIGH 202, MP_HIGH 204 and low side drive transistors MN_LOW 206 and MP_LOW 208 so that the output 238 is alternately driven to +/−HV. As illustrated, a first half cycle of the ultrasonic drive signal is generated by asserting T1 to turn on drive transistors MN_HIGH 202 and MP_HIGH 204 while negating T2 to turn off drive transistors MN_LOW 206 and MP_LOW 208. A second half cycle of the ultrasonic drive signal is generated by asserting T2 to turn on drive transistors MN_LOW 206 and MP_LOW 208 while negating T1 to turn off drive transistors MN_HIGH 202 and MP_HIGH 204. Any desired number of output signal cycles can be generated in this manner.

In period 304, some embodiments pull the output 238 to ground between the assertions of T1 and T2 by enabling the output clamp. Some embodiments generate unipolar pulses by alternately enabling the output clamp (asserting T3 and/or T4) and asserting one of T1 and T2 to drive +HV or −HV.

In period 306, which may occur between high voltage ultrasonic bursts or when generation of ultrasonic drive is terminated, the transmitter 200 returns to shunt mode as described above. As previously explained, by bringing signals T1 and T2 to a common voltage during this period, the power dissipated in the bias resistors R0-R3 210-216 is advantageously reduced.

Figure 4:
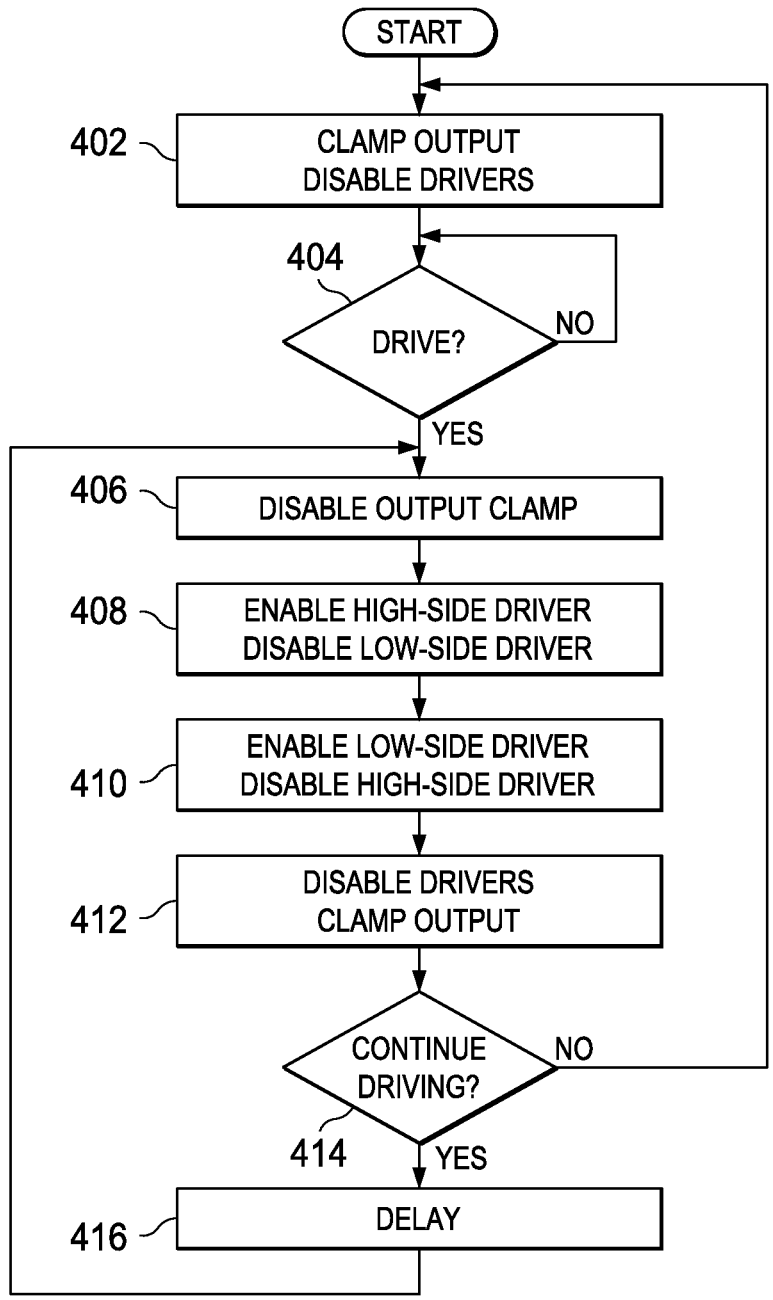
FIG. 4 shows a flow diagram for a method for generating high voltage ultrasonic drive signals in accordance with various embodiments.

FIG. 4 shows a flow diagram for a method for generating a high voltage ultrasonic drive signal in accordance with various embodiments. Though depicted sequentially as a matter of convenience, at least some of the actions shown can be performed in a different order and/or performed in parallel. Additionally, some embodiments may perform only some of the actions shown. In block 402, the transmitter 200 is producing no ultrasonic drive signal, and consequently the shunt mode is enabled. The clamp transistors, Q11 226 and Q12 228 are turned on to clamp the output 238 to ground. The high voltage drive transistors MN_HIGH 202, MP_HIGH 204, MN_LOW 206, and MP_LOW 208 are turned off.

If transducer drive is requested, in block 404, then the clamp transistors Q11 226 and Q12 228 holding the output 238 to ground are turned off in block 406.

In block 408, the positive portion of the high voltage ultrasonic drive signal is generated. +HV drive is enabled by turning on drive transistors MN_HIGH 202 and MP_HIGH 204, and −HV drive is disabled by turning off drive transistors MN_LOW 206, and MP_LOW 208. The negative portion of the high voltage ultrasonic drive signal is generated in block 410, where +HV drive is disabled by turning off drive transistors MN_HIGH 202 and MP_HIGH 204, and −HV drive is enabled by turning on drive transistors MN_LOW 206, and MP_LOW 208. Embodiments may repetitively perform the operations of blocks 408 and 410 to generate any number of cycles of the high voltage ultrasonic drive signal. Some embodiments perform the operations of blocks 412 and 406 between blocks 408 and 410 to pull the output 238 to ground before transitioning the output 238 from +HV to −HV and vice versa. Some embodiments, repeat blocks 406, 412, and one of blocks 408 and 410 to generate unipolar output pulses.

In block 412, ultrasonic drive is not required for at least a predetermined time period and the transmitter output 238 is clamped to ground. The drive transistors MN_HIGH 202, MP_HIGH 204, MN_LOW 206, and MP_LOW 208 are turned off to disable high voltage drive onto output 238, and to advantageously reduce transmitter 200 quiescent power consumption. As explained above the duty cycle of the high voltage transmitter may be approximately 1% in some embodiments, thus reducing current flow in the bias resistors R0-R3 210-216 when the transmitter 200 is disabled can result in substantial power reduction. To discharge the output 238 (i.e., to clamp the output to ground), the clamp transistors Q11 226 and Q12 228 are turned on.

If, in block 414, transducer drive is to be continued, that is, another ultrasonic signal burst is required, then after a predetermined time delay, in block 416, signal generation continues in block 406 as described above.

The above discussion is meant to be illustrative of the principles and various embodiments of the present invention. Numerous variations and modifications will become apparent to those skilled in the art once the above disclosure is fully appreciated. For example, while embodiments of the present disclosure have been described by reference to a high voltage ultrasound transmitter, those skilled in the art will recognize that embodiments of the invention can be applied to other apparatus that may benefit from symmetry. Thus, embodiments of the present disclosure are not limited to high voltage transmitter applications. It is intended that the following claims be interpreted to embrace all such variations and modifications.

What is claimed is:

1. An ultrasound transmitter, comprising:
    a high side driver and a low side driver, wherein each of the a high side driver and a low side driver comprising an N-type field effect transistor (FET) serially coupled to a P-type FET, where, the N-type FET and P-type FET of each of the high side driver and the low side driver configured to switch current to an output of the driver in response to a driver switching control signal;
    buffer drivers comprising inputs and outputs where inputs are coupled to the bias network and outputs are coupled to both the high side and the low side drivers;
    a bias network that substantially equalizes the voltage drop across the N-type FET and the P-type FET of the high side and the low side drivers;
    wherein the bias network further comprises:
    a first, second, third and fourth resistance coupled in series between the first input to the second input on an input side of the ultrasound transmitter, and coupled between the gate of the N-type FET of the high side driver and the gate of the P-type FET of the low side driver on an output side of the ultrasound transmitter,
    wherein a first buffer is coupled between the first resistance and the second resistance and the gate of the high side P-type FET;
    wherein a second buffer is coupled between the third resistance and the fourth resistance and the gate of the low side N-type FET; and
    wherein a node between the second resistor and the third resistor is coupled to a node between the high side driver and the low side driver;
    wherein current flow through the bias network becomes substantially zero when the first and second drivers are disabled; and
    wherein activation of the high side driver drives the ultrasound transmitter output to a first voltage and activation of the low side driver drives the ultrasound transmitter output to a second voltage, said activations producing a high voltage ultrasonic drive signal at the ultrasound transmitter output preserving a symmetry of the high-side and the low-side.

2. The ultrasound transmitter of claim 1, wherein the P-type FET of the high side driver is connected to the ultrasound transmitter output and the N-type FET of the high side driver switches voltage to the P-type FET.

3. The ultrasound transmitter of claim 1, wherein one of the high side and low side drivers is activated while the other of the high side driver and low side drivers is inactivated.

4. The ultrasound transmitter of claim 1, wherein the N-type FET of the low side driver is connected to the transmitter output and the P-type FET of the low side driver switches voltage to the N-type FET.

5. The ultrasound transmitter of claim 1, further comprising the first buffer coupled between a first node of the bias network and the high side driver, and the second buffer coupled between a second node of the bias network and the low side driver.

6. The ultrasound transmitter of claim 1, wherein the transmitter is disabled by driving high side and low side driver control inputs to a voltage of substantially zero.

7. The ultrasound transmitter of claim 1, wherein the N-type FET of the high side driver is coupled between the P-type FET of the high side driver and a positive power supply, and the P-type FET of the low side driver is coupled between the N-type FET of the low side driver and a negative power supply.

8. A method for providing a high voltage ultrasonic drive signal, comprising:
    a stacked field effect transistors (FET) with high side and a low side drivers where each of the both high side driver and low side drivers further comprise N-type FET and P-type FET connected in series,
    activating each of the high side N-type FET and a high side P-type FET drive an output node to a first voltage in response to a driver switching control signal;
    deactivating each of a low side N-type FET and a P-type FET while the high side N-type FET and the P-type FET are activated, where the low side N-type FET and a low side P-type FET drive the output node to a second voltage when activated in response to a driver switching control signal;
    reducing current flow in a bias network by deactivating both the high side and the low side N-type FETs as well as both the high side and low side P-type devices FETs;
    preserving a symmetry of the high-side and the low-side; and
    providing a high voltage ultrasonic drive signal:
    wherein the bias network further comprises:
    a first, second, third and fourth resistance coupled in series between the first input to the second input on an input side of the ultrasound transmitter, and coupled between the gate of the N-type FET of the high side driver and the gate of the P-type FET of the low side driver on an output side of the ultrasound transmitter,
    wherein a first buffer is coupled between the first resistance and the second resistance and the gate of the high side P-type FET;
    wherein a second buffer is coupled between the third resistance and the fourth resistance and the gate of the low side N-type FET; and wherein a node between the second resistor and the third resistor is coupled to a node between the high side driver and the low side driver.

9. The method of claim 8, further comprising driving a control input of the high side N-type FET and the low-side P-type FET to a third voltage to deactivate the FETs.

10. An ultrasound imaging system, comprising:
an ultrasonic signal transducer that converts an electrical signal into an acoustical signal;
a signal transmitter coupled to the transducer, the transmitter comprising a high-side driver that comprises a first set of stacked complementary drive transistors and a low side driver that comprises a second set of stacked complementary drive transistors, each driver comprising an N-type field effect transistor (FET) serially coupled to a P-type FET, the N-type FET and the P-type FET of each high side and low side driver configured to switch current to an output of the driver in response to a common driver switching control signal; and
a bias network that substantially equalizes the voltage drop across the N-type FET and the P-type FET of the low side driver and the high side driver, wherein the current flow in the bias network is reduced by disabling the high-side and the low-side drivers,
wherein the bias network further comprises:
first, second, third and fourth resistance coupled in series between the first input to the second input on an input side of the ultrasound transmitter, and coupled between the gate of the N-type FET of the high side driver and the gate of the P-type FET of the low side driver on an output side of the ultrasound transmitter,
wherein a first buffer is coupled between the first resistance and the second resistance and the gate of the high side P-type FET;
wherein a second buffer is coupled between the third resistance and the fourth resistance and the gate of the low side N-type FET; and
wherein a node between the second resistor and the third resistor is coupled to a node between the high side driver and the low side driver,
wherein activation of the high side driver drives the ultrasound transmitter output to a first voltage and activation of the low side driver drives the ultrasound transmitter output to a second voltage, said activations producing a high voltage ultrasonic drive signal at the ultrasound transmitter output preserving a symmetry of the high-side and the low-side.

11. The ultrasound imaging system of claim 10, wherein the high-side driver and the low-side driver are disabled by driving a control input of each driver to a common voltage.

12. The apparatus of claim 1, wherein the leakage current becomes 0 A when the output drivers are disabled.

* * * * *